US00PP28461P3

(12) United States Plant Patent
de Bruijn

(10) Patent No.: US PP28,461 P3
(45) Date of Patent: Sep. 26, 2017

(54) ***ASTILBE* PLANT NAMED 'SMILE AT ME'**

(50) Latin Name: *Astilbe arendsii*
Varietal Denomination: Smile At Me

(71) Applicant: Tom de Bruijn, 's-Gravenzande (NL)

(72) Inventor: Tom de Bruijn, 's-Gravenzande (NL)

( * ) Notice: Subject to any disclaimer, the term of this patent is extended or adjusted under 35 U.S.C. 154(b) by 0 days.

(21) Appl. No.: 14/998,536

(22) Filed: Jan. 16, 2016

(65) Prior Publication Data

US 2017/0208728 P1 Jul. 20, 2017

(51) Int. Cl.
*A01H 5/02* (2006.01)

(52) U.S. Cl.
USPC ..... Plt./407

(58) Field of Classification Search
USPC ..... Plt./407
CPC ..... A01H 5/02
See application file for complete search history.

(56) References Cited

PUBLICATIONS https://has.nl/nl/showcase/studenten-helpen-astilbe-'look-me'-van-lucassen-naar-hoger-niveau; 2 pages; no date.*

* cited by examiner

*Primary Examiner* — Kent L Bell
(74) *Attorney, Agent, or Firm* — C. A. Whealy

(57) ABSTRACT

A new and distinct cultivar of *Astilbe* plant named 'Smile At Me', characterized by its compact and broadly upright plant habit; dark green leaves; freely and uniformly flowering habit; dark pink-colored flowers that are positioned just above the foliar plane on strong reddish brown-colored stems; and good container and garden performance.

3 Drawing Sheets

Botanical designation: *Astilbe arendsii.*
Cultivar denomination: 'SMILE AT ME'.

BACKGROUND OF THE INVENTION

The present invention relates to a new and distinct cultivar of *Astilbe*, botanically known as *Astilbe arendsii* and hereinafter referred to by the name 'Smile At Me'.

The new *Astilbe* plant is a product of a planned breeding program conducted by the Inventor in 's-Gravenzande, The Netherlands. The objective of the breeding program was to create new uniform and freely flowering *Astilbe* plants with attractive leaf and flower coloration.

The new *Astilbe* plant originated from a cross-pollination made by the Inventor in 2010 in 's-Gravenzande, The Netherlands, of two unnamed selections of *Astilbe arendsii*, not patented. The new *Astilbe* plant was discovered and selected by the Inventor as a single flowering plant from within the progeny of the stated cross-pollination in a controlled greenhouse environment in 's-Gravenzande, The Netherlands in 2012.

Asexual reproduction of the new *Astilbe* plant by vegetative divisions in a controlled environment in Afferden, The Netherlands since December, 2013 has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Smile At Me'. These characteristics in combination distinguish 'Smile At Me' as a new and distinct *Astilbe* plant:

1. Compact and broadly upright plant habit.
2. Dark green-colored leaves.
3. Freely and uniformly flowering habit.
4. Dark pink-colored flowers that are positioned just above the foliar plane on strong reddish brown-colored stems.
5. Good container and garden performance.

Plants of the new *Astilbe* differ primarily from plants of the parent selections in the following characteristics:

1. Plants of the new *Astilbe* are shorter and more compact than plants of the parent selections.
2. Plants of the new *Astilbe* are more freely flowering than plants of the parent selections.

Plants of the new *Astilbe* can be compared to plants of *Astilbe arendsii* 'Gloria', not patented. In side-by-side comparisons conducted in Hillegom, The Netherlands, plants of the new *Astilbe* and 'Gloria' differed in the following characteristics:

1. Plants of the new *Astilbe* were shorter and more compact than plants of 'Gloria'.
2. Plants of the new *Astilbe* were bushier and denser than plants of 'Gloria'.
3. Inflorescences of plants of the new *Astilbe* were positioned just above foliar plane whereas inflorescences of plants of 'Gloria' were positioned much higher than the foliar plane.

4. Plants of the new *Astilbe* were more freely flowering than plants of 'Gloria'.
5. Inflorescences of plants of the new *Astilbe* and 'Gloria' differed in flowering stem color as plants of 'Gloria' had green-colored flowering stems.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Smile At Me' grown in a container.

The photograph on the second sheet is a close-up view of typical leaflets of 'Smile At Me'.

The photograph on the third sheet is a close-up view of typical inflorescences of 'Smile At Me'.

DETAILED BOTANICAL DESCRIPTION

The aforementioned photographs and following observations, measurements and values describe plants grown in 22-cm containers during the late summer and early autumn in an outdoor nursery in Afferden, The Netherlands and under cultural practices typical of commercial *Astilbe* production. During the production of the plants, day temperatures ranged from 14° C. to 32° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe arendsii* 'Smile At Me'.

Parentage:

*Female, or seed, parent*.—Unnamed *Astilbe arendsii* seedling selection, not patented.

*Male, or pollen, parent*.—Unnamed *Astilbe arendsii* seedling selection, not patented.

Propagation:

*Type*.—By divisions.

*Time to initiate roots*.—About three weeks at temperatures about 20° C.

*Root description*.—Thick, fleshy.

*Rooting habit*.—Freely branching; dense.

Plant description:

*Plant form and growth habit*.—Herbaceous perennial; compact and broadly upright plant habit with inflorescences held just above the foliar plane; plant shape broadly triangular; flowering stems and leaves basal; freely flowering with numerous basal branches developing per plant; low vigor; freely and uniformly flowering habit.

*Growth rate*.—Slow-growing; from divisions, about ten months are required to produce fully-grown flowering plants in containers.

*Plant height* (*soil level to top of foliar plane*).—About 22 cm.

*Plant height* (*soil level to top of inflorescences*).—About 12 cm.

*Plant width* (*spread*).—About 30.5 cm.

*Stem description*.—Length: About 2 cm. Diameter: About 4 mm. Strength: Strong, sturdy. Texture: Sparsely pubescent. Luster: Moderately glossy. Color: Close to N199C.

Leaf description:

*Arrangement*.—Alternate in basal rosettes; biternately compound; about 9 to 27 leaflets per leaf.

*Leaf length* (*excluding petiole*).—About 15.4 cm.

*Leaf width*.—About 15.5 cm.

*Leaflet length*.—About 5.2 cm.

*Leaflet width*.—About 2.1 cm.

*Leaf shape*.—Roughly deltoid to broadly ovate in outline.

*Leaflet shape*.—Ovate.

*Leaflet apex*.—Narrowly apiculate.

*Leaflet base*.—Attenuate.

*Leaflet margin*.—Serrate to biserrate.

*Leaflet texture, upper and lower surfaces*.—Moderately pubescent; rough.

*Leaflet luster, upper surface*.—Glossy.

*Leaflet luster, lower surface*.—Somewhat glossy.

*Leaflet venation pattern*.—Pinnate.

*Leaflet color*.—Developing leaflets, upper surface: Close to 146A tinged with close to 183B. Developing leaflets, lower surface: Close to 199A; venation, close to 187C. Fully expanded leaflets, upper surface: Slightly darker than between NN137B and 147A; venation, close to 148A. Fully expanded leaflets, lower surface: Close to 147B; venation, close to 176B to 176C.

*Leaf petiole length*.—About 4.5 cm.

*Leaf petiole diameter*.—About 2 mm.

*Leaflet petiole length*.—About 8 mm.

*Leaflet petiole width*.—About 1 mm.

*Leaf and leaflet petiole texture, upper and lower surfaces*.—Smooth, glabrous.

*Leaf and leaflet petiole color, upper and lower surfaces*.—Close to 187B.

Flower description:

*Flower type and flowering habit*.—Single rotate flowers arranged on terminal panicles; flowers face upright, outwardly or drooping depending on position on the inflorescence; panicles broadly conical in shape; freely and uniformly flowering habit with about 2,500 flowers developing per inflorescence.

*Fragrance*.—Faint; sweet, pleasant.

*Natural flowering season*.—Plants begin flowering about ten months after planting; continuously flowering from early to late summer in The Netherlands.

*Postproduction longevity*.—Flowers last about ten days on the plant; flowers persistent.

*Flower buds*.—Height: About 2 mm. Diameter: About 1.5 mm. Shape: Elliptic. Color: Close to 59D.

*Inflorescence height*.—About 24.5 cm.

*Inflorescence diameter*.—About 17.7 cm.

*Flower diameter*.—About 6 mm.

*Flower depth*.—About 4 mm.

*Petals*.—Quantity per flower: Typically five in a single whorl. Length: About 3 mm. Lobe width: About 0.5 mm. Shape: Oblanceolate. Apex: Acute. Margin: Entire. Texture, upper and lower surfaces: Smooth, glabrous. Luster, upper and lower surfaces: Dull. Color: Developing petals, upper and lower surfaces: Close to 70D. Fully expanded petals, upper and lower surfaces: Close to 73C; color becoming closer to 73D with development.

*Sepals*.—Quantity per flower: Typically five in a single whorl, fused towards the base; campanulate-shaped calyx. Length: About 2.5 mm. Width: About 0.8 mm. Shape: Ovate. Apex: Acute. Margin: Entire. Texture, upper and lower surfaces: Smooth, glabrous. Luster, upper and lower surfaces: Dull. Color: Developing sepals, upper and lower surfaces: Close to N66B. Fully expanded sepals, upper surface: Close to 67D; towards the apex, close to 63A. Fully expanded sepals, lower surface: Close to 67B; towards the apex, close to 63A.

*Peduncles*.—Length: About 23.6 cm. Diameter: About 2 mm. Angle: Erect to about 45° from vertical. Strength: Strong. Texture: Smooth, glabrous. Color: Close to 174A.

*Pedicels*.—Length: About 2 mm. Diameter: About 0.5 mm. Angle: About 45° from peduncle axis. Strength: Moderately strong. Texture: Smooth, glabrous. Color: Close to 59A.

*Reproductive organs*.—Stamens: Quantity per flower: Typically ten. Filament length: About 2 mm. Filament color: Close to 70D. Anther shape: Ovate, basifixed. Anther length: About 0.5 mm. Anther color: Close to 186D. Pollen amount: Scarce. Pollen color: Close to 156D. Pistils: Quantity per flower: Typically two. Pistil length: About 2 mm. Stigma shape: Club-shaped. Stigma color: Close to 70D. Style length: About 1.75 mm. Style color: Close to 70C. Ovary color: Close to 70C.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures of about 35° C. Plants of the new *Astilbe* have been observed to be hardy to USDA Hardiness Zone 5.

It is claimed:

1. A new and distinct *Astilbe* plant named 'Smile At Me' as illustrated and described.

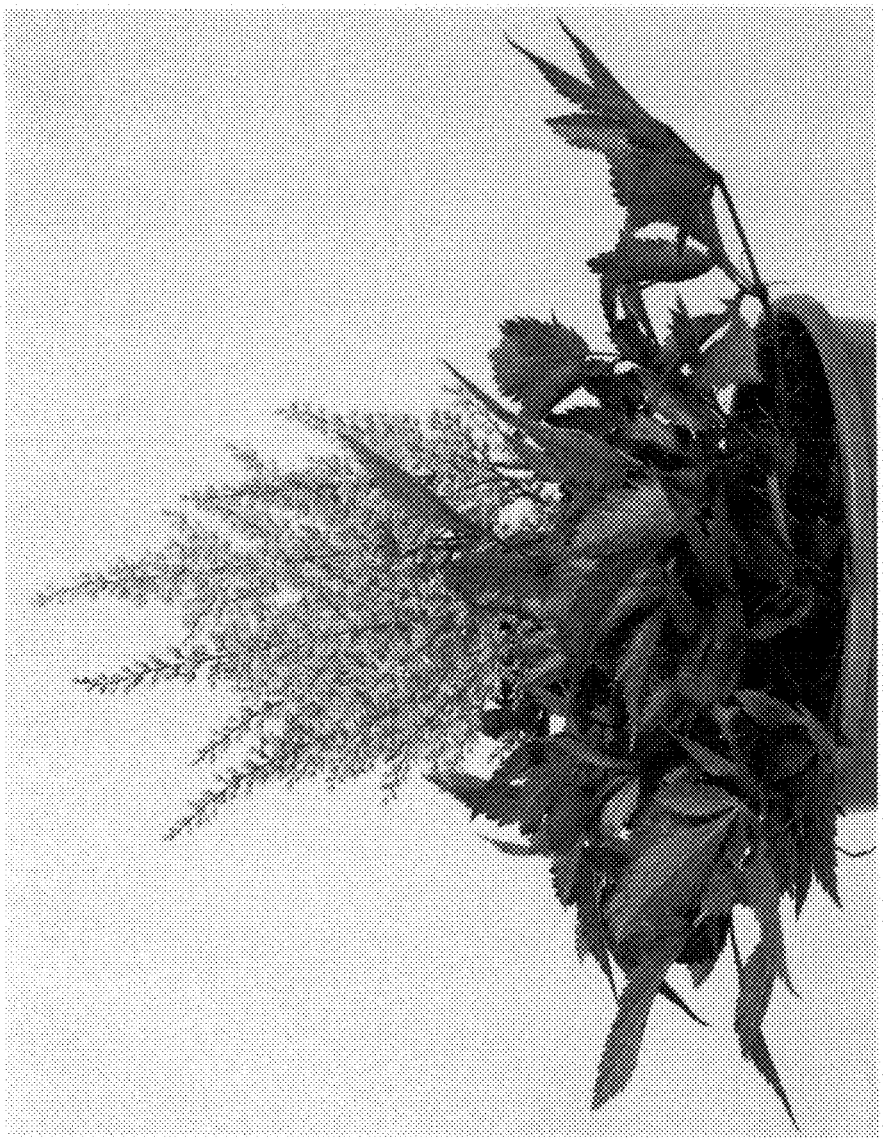

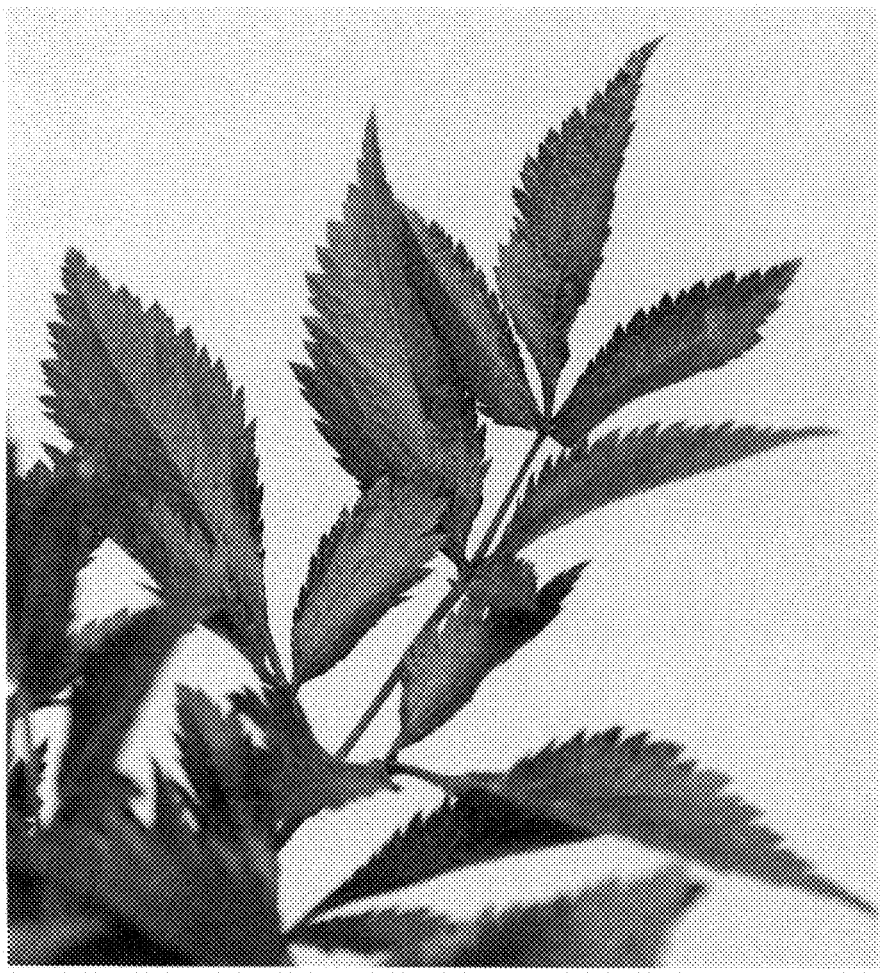

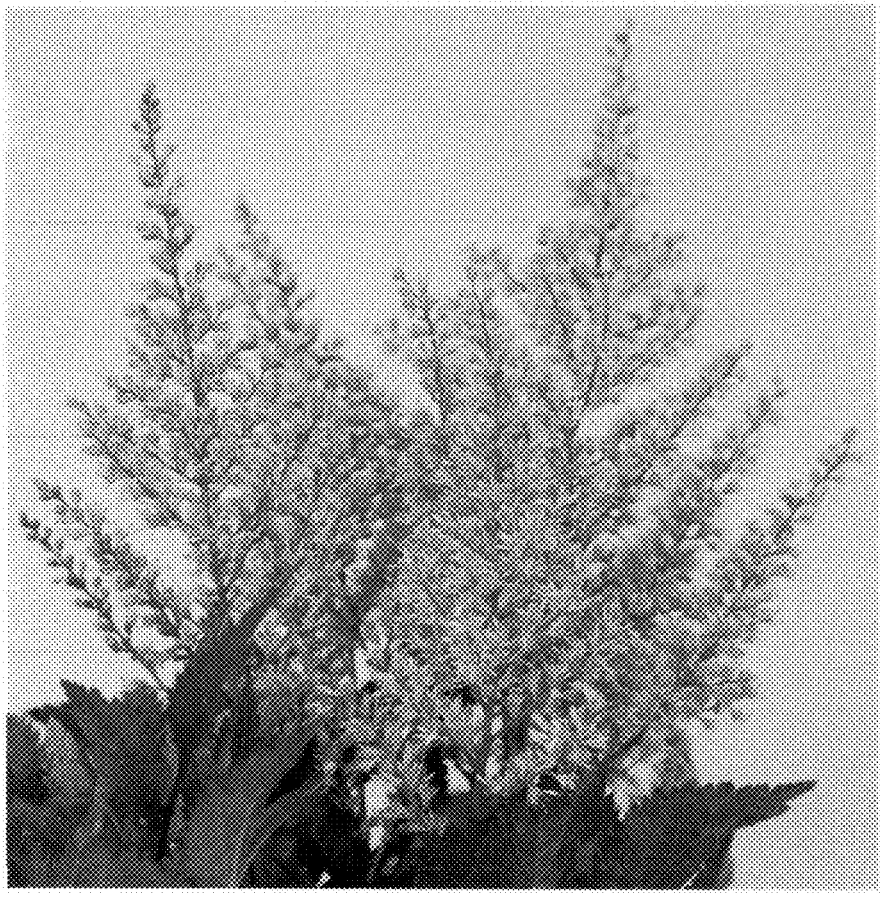

* * * * *